US005785666A

United States Patent [19]
Costello et al.

[11] Patent Number: 5,785,666
[45] Date of Patent: Jul. 28, 1998

[54] PORTABLE ELECTRONIC DATA COLLECTION APPARATUS FOR MONITORING MUSCULOSKELETAL STRESSES

[75] Inventors: Kevin J. Costello, Sea Cliff; Chandra Nair, Glen Cove; Cynthia Roth, Massapequa; Dennis A. Mitchell, Huntington, all of N.Y.

[73] Assignee: Ergonomic Technologies Corporation, Oyster Bay, N.Y.

[21] Appl. No.: 550,676

[22] Filed: Oct. 31, 1995

[51] Int. Cl.⁶ .......................... A61B 5/103; A61B 5/117; A61B 5/04; A61B 5/0265
[52] U.S. Cl. .......................... 600/595; 600/409; 600/546; 600/587
[58] Field of Search .................... 128/782, 774, 128/733, 653.1; 600/409, 546, 587, 595

[56] References Cited

U.S. PATENT DOCUMENTS

| 4,250,380 | 2/1981 | Iyeta . |
| 4,442,606 | 4/1984 | Graham et al. . |
| 4,450,843 | 5/1984 | Barney et al. . |
| 4,650,996 | 3/1987 | Maehara et al. . |
| 4,676,002 | 6/1987 | Slocum . |
| 4,986,280 | 1/1991 | Marcus et al. . |
| 5,086,785 | 2/1992 | Gentile et al. . |
| 5,163,228 | 11/1992 | Edwards et al. . |
| 5,166,462 | 11/1992 | Suzuki et al. . |
| 5,216,193 | 6/1993 | Masubuchi . |
| 5,280,265 | 1/1994 | Kramer et al. . |
| 5,313,968 | 5/1994 | Logan et al. . |
| 5,316,017 | 5/1994 | Edwards et al. . |
| 5,513,651 | 5/1996 | Cusimano et al. ............. 128/782 |

*Primary Examiner*—Aaron J. Lewis
*Assistant Examiner*—Dinh X. Nguyen
*Attorney, Agent, or Firm*—Morgan & Finnegan, L.L.P.

[57] ABSTRACT

A portable biofeedback apparatus and method for simultaneously gathering information regarding more than one type of musculoskeletal stress. The apparatus has at least two different types of user-selectable sensors for converting different kinds of musculoskeletal activities into electrical signals. An analog-to-digital converter samples the electrical signals at predetermined rates. A memory receives and stores the digital signals. A processor centrally controls the collection, sampling, display and transmittal of the digital data. Magnitudes of the digital signals are simultaneously and in real-time graphically portrayed as a function of time.

11 Claims, 5 Drawing Sheets

PORTABLE ELECTRONIC DATA COLLECTION APPARATUS FOR MONITORING MUSCULOSKELETAL STRESSES

TECHNICAL FIELD

The present invention relates generally to portable biofeedback units, and, more particularly, to a portable electronic biofeedback apparatus and method for collecting and displaying simultaneously data regarding levels of several types of musculoskeletal stresses in the human body.

BACKGROUND OF THE INVENTION

In recent years, the number of reports of work-related musculoskeletal disorders such as cumulative trauma disorders (CTDs) (also called repetitive stress injuries (RSIs)) has multiplied. Some risk factors which contribute to the development of RSIs include applied force, acceleration, velocity and repetition rate of a task. A common RSI is carpal tunnel syndrome, a condition characterized by a thickening of the protective sheaths which surround each tendon in the wrist which control finger movement. Carpal tunnel syndrome may be caused by repetitive flexing and extension of the wrist.

Workers are susceptible to injury from the sustained repetitive activities which define some jobs. Typing is an example of a job which requires a person to perform the same motion pattern every few seconds, as are jobs which require the use of vibrating equipment, and jobs in which workers repeatedly handle heavy objects.

Increasingly, employers are examining those jobs and workpieces that have risk factors for RSIs to determine the extent to which RSIs or the potential for RSIs are present. It is therefore desirable to identify the movements or stresses on each job or within each workpiece which may present patterns of harmful physical stress, and to quantitatively measure and analyze the levels of physical stress while the potentially harmful activity is being performed.

A variety of biofeedback devices are available to aid in gathering data pertaining to musculoskeletal stresses. For example, electromyographic sensors and force sensing resistors measure muscular activity and force, respectively, and position sensors measure posture. Typically, biofeedback units utilize one type of device to translate a particular physical activity of a person into electric signals, and display representations of the signals in understandable form to the person whose activity is being monitored.

One type of well known biofeedback unit measures electromyographic (EMG) activity, that is, the electrical activity of a muscle during contraction, via electrodes placed on the skin over a muscle or a group of muscles to be monitored. Another kind of biofeedback unit, a goniometer, provides feedback regarding the angular position of a joint of the human body, i.e., posture. It is futher widely known to sense vibrations by attaching accelerometers to parts of the body, and to sense levels of force between a portion of a person's body, such as the fingertips, and another object, such as a keyboard, with variable force sensing resistors (FSRs). EMG electrodes, goniometers, accelerometers, and FSRs are all items which are available off-the-shelf from various sources.

Portable biofeedback systems which are capable of gathering multiple types of musculoskeletal stress data simultaneously, however, have not heretofore been available. A biofeedback unit for measuring, for example, pressure, muscle activity and posture simultaneously offers the advantage that a researcher may determine at a glance the muscle effort and posture required to sustain a specific force during performance of a task.

In addition, it is awkward and time consuming to utilize separate portable units to measure more than one type of activity, and many biofeedback systems require a user to perform extensive and complicated calibration procedures before each use—such systems are generally not suitable for use at a worksite to measure on-the-job musculoskeletal stresses, nor are they useful to quickly test the ergonomics and/or efficacy of a workpiece's design.

Advantages and novel features of the invention will be set forth in the description which follows, and in part will become apparent to those skilled in the art upon examination of the following or may be learned by practice of the invention. The advantages of the invention may be realized and attained by means of the instrumentalities and combinations particularly pointed out in the appended claims.

SUMMARY OF THE INVENTION

According to the present invention, the foregoing and other disadvantages are ameliorated by a portable electronic data collection apparatus including dissimilar sensors for converting musculoskeletal activities into electrical signals, each sensor being input to a channel. An Analog-to-digital (A/D) converter samples the electrical signals from a user-selected channel at a predetermined rate, such that digital values of the electrical signals are obtained. A processor centrally controls the collection and display of the digital data. A memory in communication with the processor receives and stores the digital values. Some general features of the preferred embodiment include a first visual display, which may be a computer monitor, for simultaneously graphing magnitudes of the digital values of the user-selected channel as a function of time.

A second visual display, which may be a liquid crystal display, may show a user of the unit a real-time numeric representation of the levels of musculoskeletal activities being monitored.

The memory may communicate with the processor via a cable, a radio-frequency connection or a portable Personal Computer Manufacturers Computer Interface Association (PCMCIA) card which is accepted by both the memory and the processor. The stored signals may be analyzed to identify potentially harmful patterns of repetitive stress.

In a preferred embodiment, the different sensors of the present invention include: surface EMG electrodes, which may be either passive (non-amplified) or amplified, for measuring electrical muscular activity; variable force sensing resistors (FSRs) for measuring force with which a portion of a person's body contacts an object; and goniometers for measuring angular positions, velocity and accelerations of a body joint. The variable sensing force resistors may be replaced by accelerometers for measuring vibrational activity.

In a still further embodiment, the unit may be calibrated by bringing an output level of the unit into substantial agreement with sampled maximum and minimum values of the various signals to be measured, presenting all output information as a percentage of the sampled maximum and minimum values.

In accordance with another aspect of the invention, a method of simultaneously collecting data regarding several different types of musculoskeletal stresses includes: simultaneously sensing EMG signals associated with at least two of the following: activity of a muscle, force signals associated with a portion of a person's body contacting an object, and angular position signals associated with a position of a body joint; sampling the signals at predetermined rates to obtain digital values of the signals at discrete points in time, the rates of sampling of the signals being optionally adjusted by a person using the unit; storing the digital values; and simultaneously and in real-time graphing magnitudes of the different digital signals as a function of time.

Still other objects and advantages of the present invention will become readily apparent to those skilled in the art from the following description, wherein only the preferred embodiment of the invention has been shown and described, simply by way of illustration of the best mode contemplated of carrying out the invention. As will be realized, the invention is capable of other and different embodiments, and its details are capable of modifications in various obvious respects, all without departing from the invention. Accordingly, the drawings and description are to be regarded as illustrative in nature, and not as restrictive.

DETAILED DESCRIPTION OF THE PREFERRED EMBODIMENT

Figure 1:
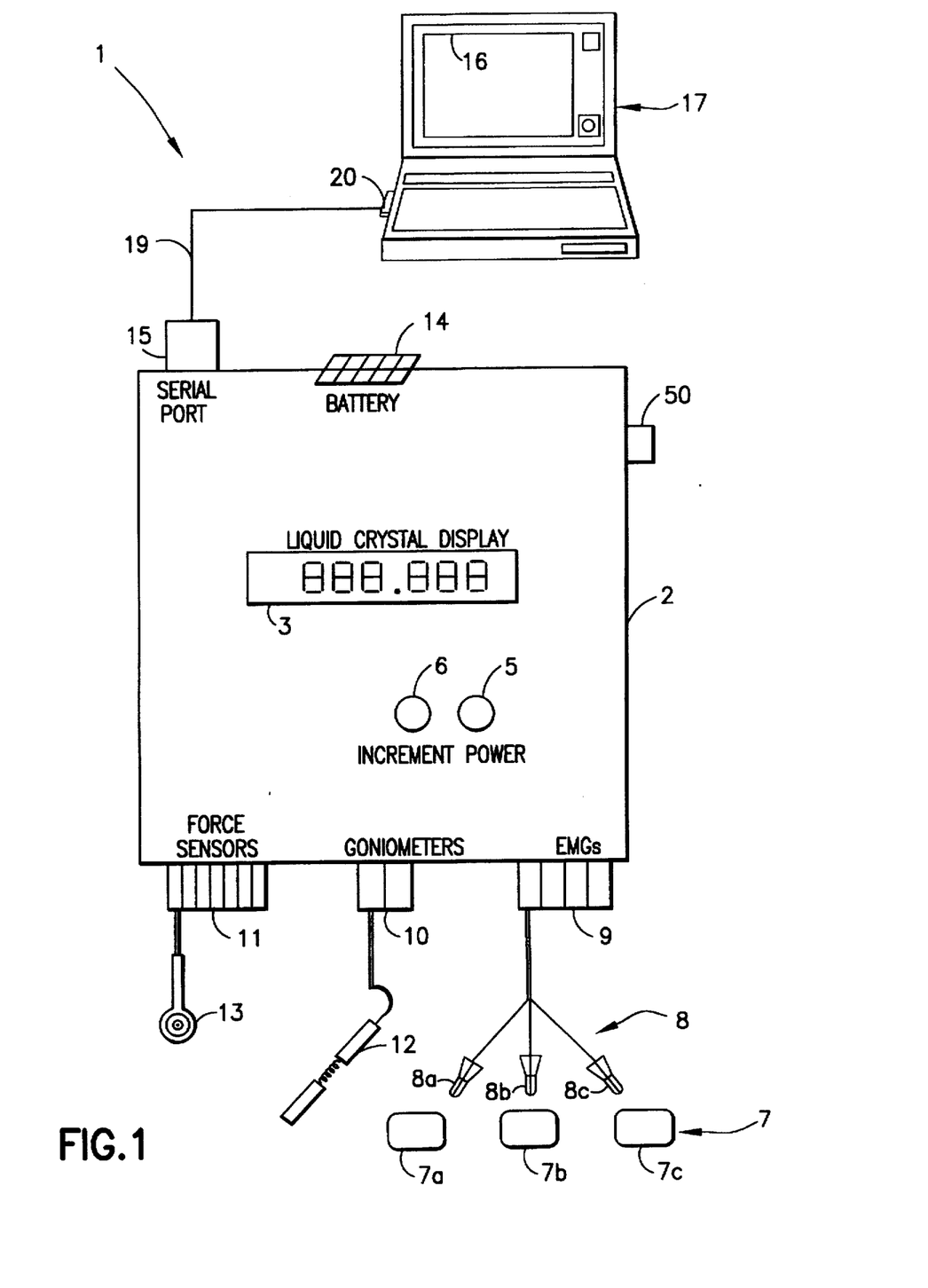
FIG. 1 illustrates a biofeedback unit constructed in accordance with the preferred embodiment of the present invention.

FIG. 1 illustrates a portable electronic data collection system 1 constructed in accordance with the preferred embodiment of the present invention. A measurement unit 2 communicates with a portable computer 17 via a cable 19 connected between a serial port 15 located on the measurement unit 2 and a serial port 20 located on the computer 17.

A plurality of dissimilar sensors, such as a force sensor 13, a goniometer 12, and an electromyographic (EMG) sensor 7 convert musculoskeletal activities into electrical signals. The force sensor 13 is a force sensing resistor (FSR), which measures the exertional force of a body part against an object. The resistance of a FSR varies in inverse proportion to an amount of force applied to the FSR.

The goniometer 12, when placed on a surface of a body joint, measures the angular deviation of the joint from a neutral position in two mutually orthogonal directions and also measures the joint's degree of rotation—an electrical signal varies as a function of the joint's position. The position measurements may be integrated to determine velocity or acceleration values which, along with position, are also potential risk factors for repetitive stress injuries (RSIs).

The EMG sensor 7 is a surface electrode which, when placed on a person's skin above a muscle, measures electrical activity generated by the muscle. The electrical signal is proportional to the amount of exertion of the muscle. The surface electrode 7 may be either of the passive type (i.e., non-amplified) or it may be amplified. Three electrodes 7 are used to measure the activity of one muscle—a muscular contraction creates a potential difference between two of the electrodes 7a, 7c, while a third electrode 7b remains at a reference potential, preferably ground. Typically, two electrodes are placed over the muscle where activity is to be measured, and a third is placed at a location away from the muscle, for example, on a bony protrusion such as an elbow. Each electrode 7a, 7b, 7c is coupled to a connector, e.g., an alligator clip 8.

The measurement unit 2 contains separate input ports for eight force sensors 11, two four-way goniometers 10 and four groups of EMG sensors 9. All or a user-selected number of the plurality of sensors may be utilized in each data gathering session. A number corresponding to the force, angular position and EMG measurements associated with each sensor in a particular group of sensors 9, 10, 11 is displayed in real-time on a liquid crystal display 3 located on the face of the measurement unit 2. An increment button 6 allows a user to choose the group of sensors 9, 10, 11, which will be displayed on the liquid crystal display 3. The unit has an on/off power button 5 which controls the battery 14, and has an A/C power adapter 50 to charge the battery 14.

The portable computer 17, preferably an IBM-compatible computer, receives and stores data corresponding to the force, angular position or EMG activity measured by each sensor, grouped by sensor type. In addition to the instantaneous measurements, time-weighted average and peak point values are continuously updated by the computer 17, and all data is simultaneously displayed graphically in real-time on a computer monitor 16. A system application program (not shown) provides a user-friendly interface for calibration and data acquisition (discussed below). Further, the program allows stored data to be analyzed to identify potentially harmful patterns and/or levels of repetitive stress. In a preferred embodiment, the system application program runs under Windows for DOS.

Figure 2A:
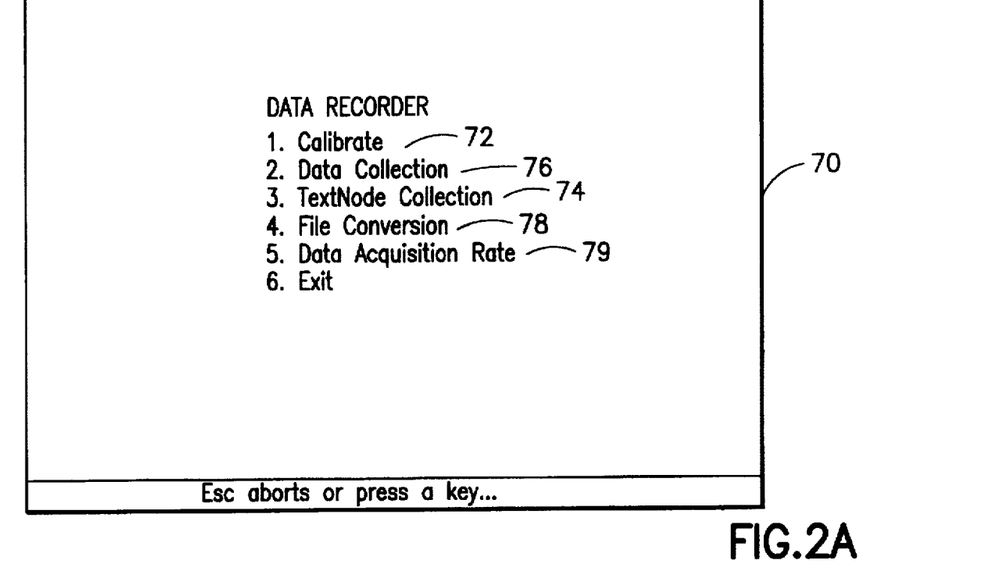
FIG. 2a illustrates a visual display which provides a main menu for a user of the biofeedback unit.

As illustrated in FIG. 2a, the system application program provides a main menu screen 70 containing options for a user to calibrate any channel 72, collect data while exhibiting it in either graphical 74 or numerical format 76, convert binary data files to an ASCII text format 78 and to change data acquisition rates 79.

Figure 2B:
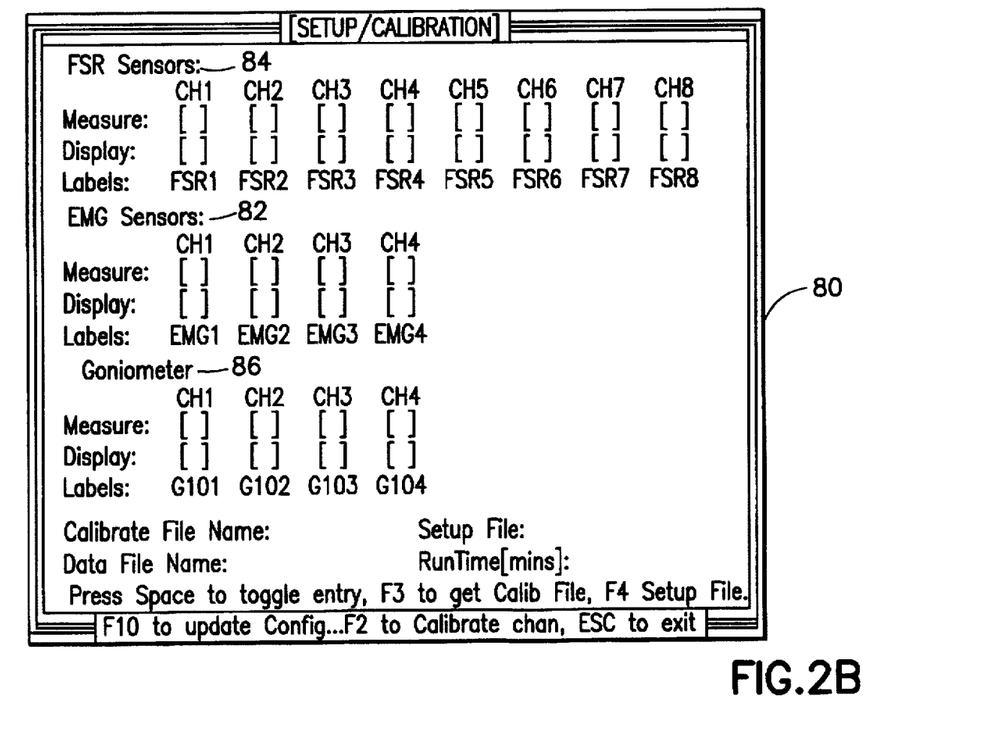
FIG. 2b illustrates a visual display which guides a user of the biofeedback unit through a calibration process.

The system application program also supports a calibration program. FIG. 2b depicts a sample screen 80 which guides a user of the system through a simple routine to initialize the EMG sensors 82, FSR sensors 84 and goniometers 86 which are being used in a measurement session. Each channel shown corresponds to one measurement input. The calibration screen is used to select the channels which will be used. The user supplies a minimum and maximum level of input to each sensor, and the calibration program uses these measurements to adjust the output level of the system such that all output information is presented as a percentage of the sampled minimum and maximum values. Software programs for implementing the foregoing are well-known in the art.

Figure 3:
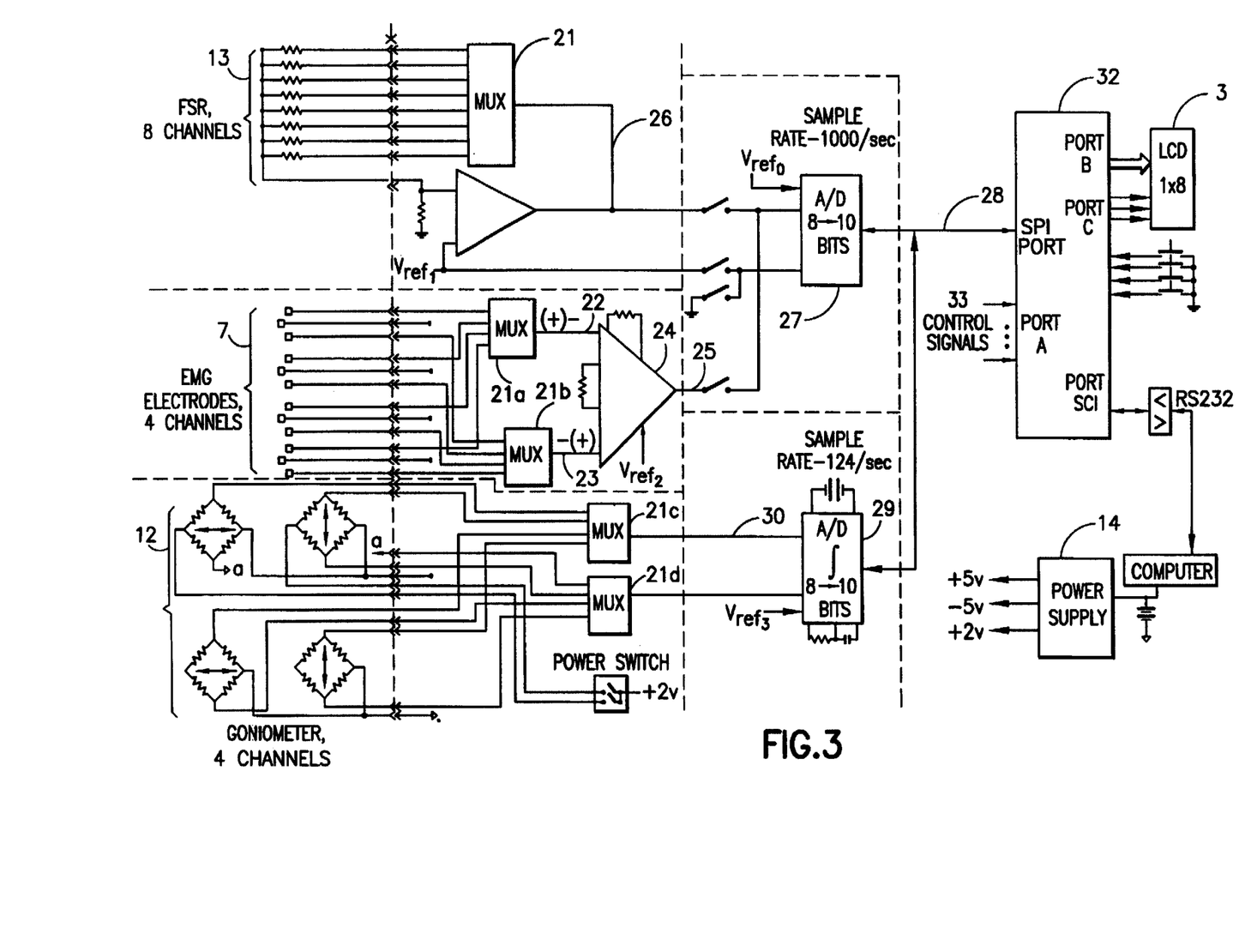
FIG. 3 is a schematic electrical diagram of the unit of FIG. 1.

FIG. 3 is an electrical diagram of the biofeedback unit depicted in FIG. 1. A plurality of multiplexers receives electrical signals from the force sensing resistors 13, EMG electrodes 7 and the goniometers 12. The outputs 22, 23 of the two multiplexers 21a, 21b associated with the EMG electrodes 7 are input to an operational amplifier 24, which provides a filtered, amplified signal 25 representing the level of contraction of a muscle over which the EMG electrodes 7 are located.

The filtered EMG signal 25 and the output 26 of the multiplexer 21 associated with the force sensing resistors 13 are input to a first analog-to-digital (A/D) converter 27 which alternately samples the signals 25, 26 at an adjustable rate up to 1000 Hz.

A second A/D converter 29 accepts electrical signals 30 from the multiplexers 21 associated with the goniometers 12, sampling the signals 30 at an adjustable rate up to 124 Hz.

A processor 32 accepts the digital signals from the first A/D converter 28 and the digital signals from the second A/D converter 31, simultaneously displaying a base-10 numerical representation of the digital signals of the selected channel on the liquid crystal display 3 and transmitting the signals via an RS-232 cable 19 to the portable computer.

The digital signals may also be transmitted to the portable computer via a radio-frequency link. Further, the unit may be adapted to accept a removable Personal Computer Manufacturers Computer Interface Association (PCMCIA) card which fits into a memory slot of the portable computer, so that a direct link to the computer is not necessary during the data gathering stage.

The processor 32 supplies control signals 33, for example a clock signal and various reference voltages, to components such as the A/D converters 27,29 and the instrumental amplifier 24. A power supply 14, such as a battery, supplies power to the processor 32.

Figure 4:
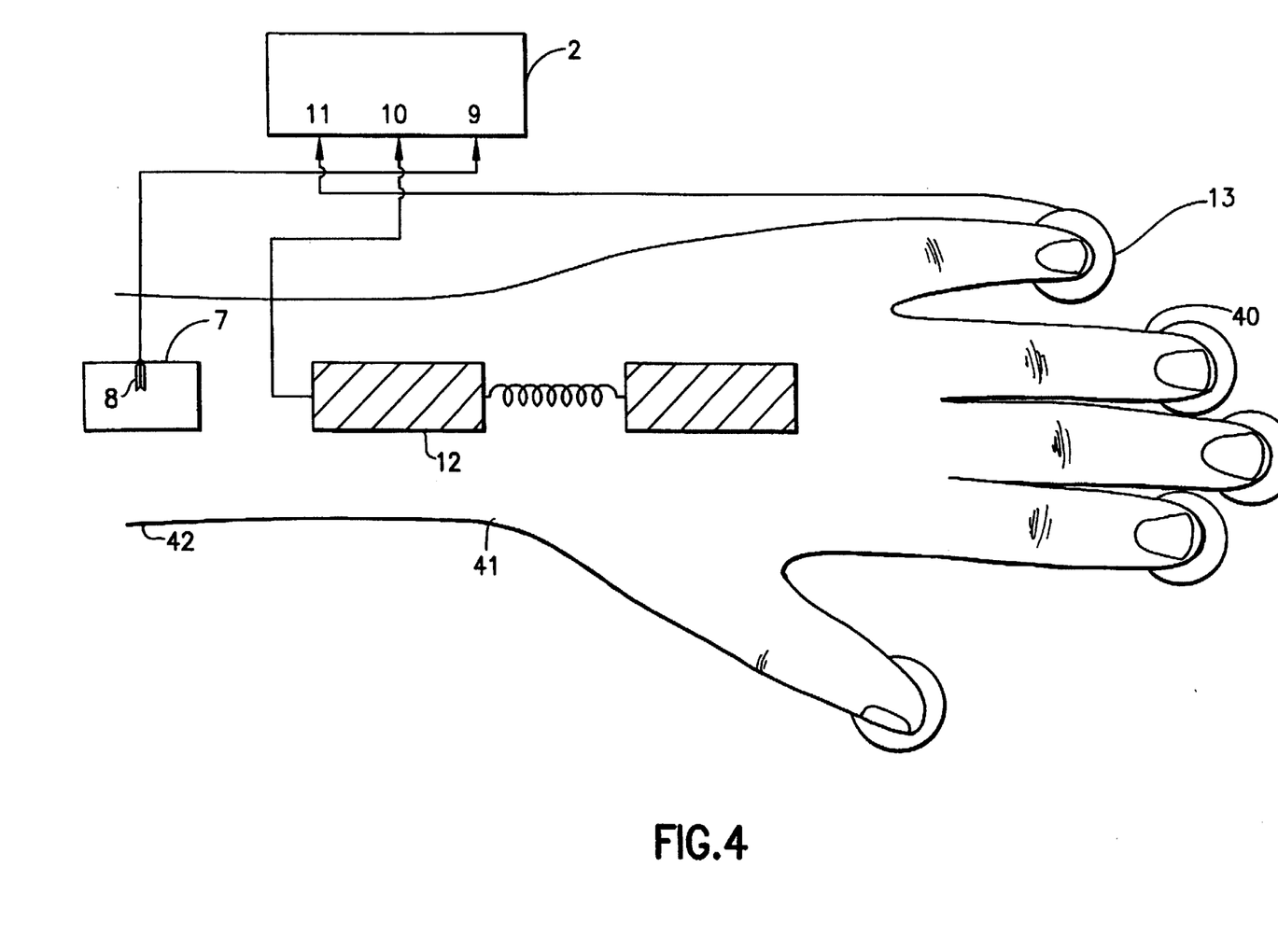
FIG. 4 is a side view of a human arm with three types of dissimilar sensors secured thereto and connected to the biofeedback unit of the present invention.

FIG. 4 is a side view of a human arm with three types of sensors secured thereto and connected to the unit 2 of the present invention. Five force sensing resistors 13 attached to fingertips 40 measure the force with which the fingertips 40 contact an object, for example a keyboard (not shown). One goniometer 12, located on the dorsal surface of the wrist 41, measures the angular deviation of the wrist from a neutral position in two mutually orthogonal directions (up-down and left-right) as well as rotation of the wrist. One set of three EMG sensors 7,8 (only one sensor shown) placed on the forearm 42 detects contraction of the underlying muscle.

Figure 5:
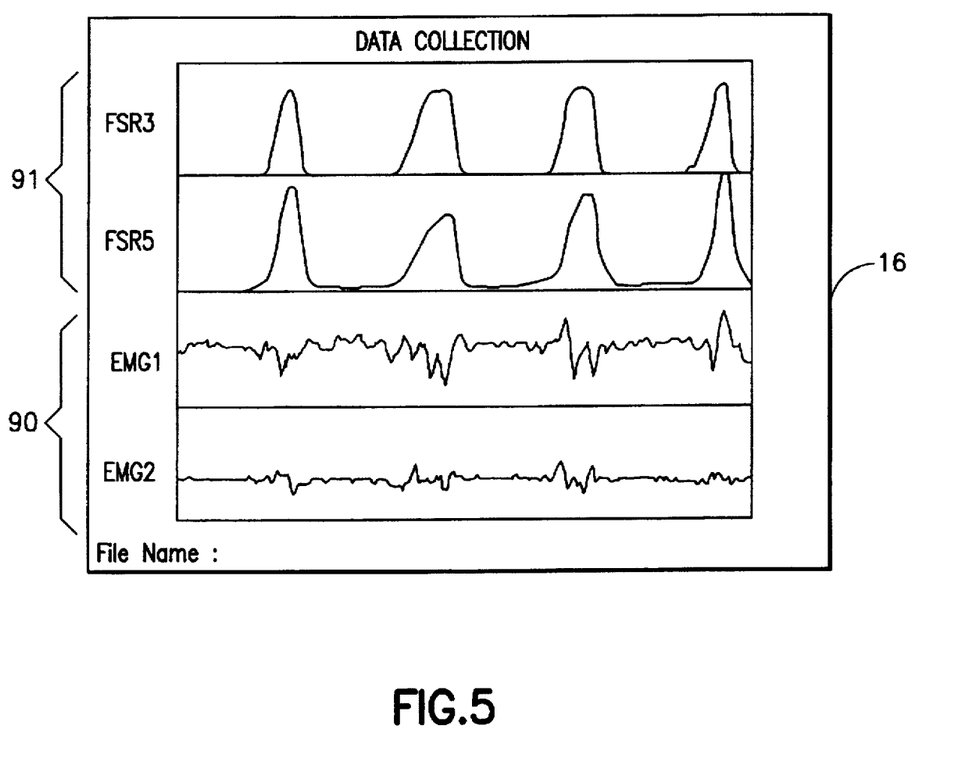
FIG. 5 illustrates a visual display which graphically depicts magnitudes of electromyographic and force signals as a function of time.

FIG. 5 shows a real-time graphical visual display of the magnitude of the force and EMG measurements associated with each sensor in a particular group of sensors 90, 91 as a function of time on the computer monitor 16. The graphical display features two channels of EMG data 90 and two channels of FSR data 91. Software modules for accomplishing the graphical display are well known to those skilled in the art.

The data shown in FIG. 5 was collected as an operator was squeezing a trigger of an electric drill with four short pulses. One EMG electrode was affixed over the finger extensor muscles while the other was located over the flexor muscles; one FSR was on the drill trigger and the other on the handle opposite the trigger under the palm of the hand.

The simultaneous graphical display allows an operator to readily observe the interrelationship between the EMG and FSR measurements, enabling a thorough analysis of the muscle effort required to sustain a specific force over a period of time. Such an analysis would not be possible if each measurement were performed and/or displayed individually.

As one skilled in the art will appreciate, this invention may be practiced with a plurality of sensors. For example, FSRs and goniometry may be used to rapidly analyze the effects of spending an amount of time in certain hazardous postures while experiencing forceful exertion, while EMG sensors and goniometry may be to helpful for identifying the physical origin of hazardous muscle stress.

We claim:

1. A portable electronic data collection apparatus for monitoring musculoskeletal stresses comprising:

a plurality of dissimilar sensors for converting a plurality of musculoskeletal activities into electrical signals, each of the plurality of sensors being an input to a channel, said plurality of dissimilar sensors including a passive surface electrode placed on a person's skin above a muscle in which activity is to be measured and in communication with a first analog-to-digital converter for measuring electromyographic signals associated with activity of the muscle, a second sensor in communication with the first analog-to-digital converter for measuring force signals associated with a portion of a human body contacting an object, a third sensor in communication with a second analog-to-digital converter for measuring angular position signals associated with the position of a body joint:

an analog-to-digital converter for sampling the electrical signals from a user-selected channel at a predetermined rate such that digital values of the electrical signals are obtained at discrete points in time;

a processor in communication with said analog-to-digital converter, for collecting the digital values of the electrical signals;

a memory in communication with said processor, said memory receiving and storing the digital values; and a first visual display in communication with said processor, said first visual display simultaneously and in real-time graphically portraying magnitudes of the digital values of the user-selected channel as a function of time.

2. A portable electronic data collection apparatus for monitoring musculoskeletal stresses comprising:

a plurality of dissimilar sensors for converting a plurality of musculoskeletal activities into electrical signals, each of the plurality of sensors being an input to a channel, said plurality of dissimilar sensors including a first sensor in communication with a first analog-to-digital converter for measuring electromyographic signals associated with activity of a muscle, a force sensing resistor located in a glove which is placed on a hand of a person and in communication with the first analog-to-digital converter for measuring force signals associated with a portion of a human body contacting an object, a third sensor in communication with a second analog-to-digital converter for measuring angular position signals associated with the position of a body joint:

an analog-to-digital converter for sampling the electrical signals from a user-selected channel at a predetermined rate such that digital values of the electrical signals are obtained at discrete points in time:

a processor in communication with said analog-to-digital converter, for collecting the digital values of the electrical signals;

a memory in communication with said processor, said memory receiving and storing the digital values: and a first visual display in communication with said processor, said first visual display simultaneously and in real-time graphically portraying magnitudes of the digital values of the user-selected channel as a function of time.

3. A portable electronic data collection apparatus for monitoring musculoskeletal stresses comprising:

a plurality of dissimilar sensors for converting a plurality of musculoskeletal activities into electrical signals, each of the plurality of sensors being an input to a channel;

an analog-to-digital converter for sampling the electrical signals from a user-selected channel at a predetermined rate such that digital values of the electrical signals are obtained at discrete points in time;

a processor in communication with said analog-to-digital converter, for collecting the digital values of the electrical signals;

a memory in communication with said processor, said memory receiving and storing the digital values;

a first visual display in communication with said processor, said first visual display simultaneously and in real-time graphically portraying magnitudes of the digital values of the user-selected channel as a function of time; and means for calibrating the apparatus so that an output level of the apparatus is in substantial agreement with measured maximum and minimum values of the electrical signals from each channel.

4. The portable electronic data collection apparatus for monitoring musculoskeletal stresses according to claim 3, wherein said means for calibrating the apparatus stores the sampled maximum and minimum values of the electrical signals from each channel for a particular person.

5. A portable electronic data collection apparatus for monitoring musculoskeletal stresses comprising:

a plurality of dissimilar sensors for converting a plurality of musculoskeletal activities into electrical signals, each of the plurality of sensors being an input to a channel;

an analog-to-digital converter for sampling the electrical signals from a user-selected channel at a predetermined rate such that digital values of the electrical signals are obtained at discrete points in time;

a processor in communication with said analog-to-digital converter, for collecting the digital values of the electrical signals;

a memory in communication with said processor, said memory receiving and storing the digital values, said memory comprising a removable PCMCIA card; and a first visual display in communication with said processor, said first visual display simultaneously and in real-time graphically portraying magnitudes of the digital values of the user-selected channel as a function of time.

6. A portable electronic data collection apparatus for monitoring musculoskeletal stresses comprising:

a plurality of dissimilar sensors for converting a plurality of musculoskeletal activities into electrical signals each of the plurality of sensors being an input to a channel:

an analog-to-digital converter for sampling the electrical signals from a user-selected channel at a predetermined rate such that digital values of the electrical signals are obtained at discrete points in time;

a processor in communication with said analog-to-digital converter, for collecting the digital values of the electrical signals;

a memory in communication with said processor, said memory receiving and storing the digital values;

a cable connecting said memory with said processor, for transmitting the digital values from said processor to said memory; and a first visual display in communication with said processor, said first visual display simultaneously and in real-time graphically portraying magnitudes of the digital values of the user-selected channel as a function of time.

7. A portable electronic data collection apparatus for monitoring musculoskeletal stresses comprising:

a plurality of dissimilar sensors for converting a plurality of musculoskeletal activities into electrical signals, each of the plurality of sensors being an input to a channel;

an analog-to-digital converter for sampling the electrical signals from a user-selected channel at a predetermined rate such that digital values of the electrical signals are obtained at discrete points in time;

a processor in communication with said analog-to-digital converter, for collecting the digital values of the electrical signals;

a memory in communication with said processor, said memory receiving and storing the digital values;

a radio-frequency connection between said memory and said processor, for transmitting the digital values from said processor to said memory; and a first visual display in communication with said processor, said first visual display simultaneously and in real-time graphically portraying magnitudes of the digital values of the user-selected channel as a function of time.

8. A portable electronic data collection apparatus for monitoring musculoskeletal stresses comprising:

a plurality of dissimilar sensors for converting a plurality of musculoskeletal activities into electrical signals, each of the plurality of sensors being an input to a channel;

an analog-to-digital converter for sampling the electrical signals from a user-selected channel at a predetermined rate such that digital values of the electrical signals are obtained at discrete points in time;

a processor in communication with said analog-to-digital converter, for collecting the digital values of the electrical signals;

a memory in communication with said processor, said memory receiving and storing the digital values;

a first visual display in communication with said processor, said first visual display simultaneously and in real-time graphically portraying magnitudes of the digital values of the user-selected channel as a function of time; and a second visual display in communication with said processor for displaying on the data collection apparatus in real-time a numeric representation of the digital values from each channel.

9. The portable electronic data collection apparatus for monitoring musculoskeletal stresses according to claim 8, wherein said second visual display comprises a liquid crystal display.

10. A portable electronic data collection apparatus for monitoring musculoskeletal stresses, comprising:

a plurality of dissimilar sensors for converting a plurality of musculoskeletal activities into electrical signals, each of the plurality of sensors being an input to a channel, the channels being grouped according to sensor type;

an analog-to-digital converter for sampling the electrical signals from at least two user-selected channels from different sensor type groups at a predetermined rate such that digital values of the electrical signals are obtained at discrete points in time;

a processor in communication with said analog-to-digital converter for collecting the digital values of the electrical signals;

a memory in communication with said processor, said memory receiving and storing the digital values;

a first visual display in communication with said processor, said first visual display simultaneously and in read-time graphically portraying magnitudes of the digital values of the user-selected channels as a function of time; and a second visual display in communication with said processor for displaying on the data collection apparatus in real-time a numeric representation of the digital values of the user-selected channels as a function of time.

11. A portable electronic data collection apparatus for monitoring musculoskeletal stresses, comprising:

means for simultaneously sensing a plurality of musculoskeletal activities and converting the sensed activities into electrical signals, each of said means for sensing comprising at least one input to a channel, the channels being grouped according to type of means for sensing;

means for sampling the electrical signals at a predetermined rate such that digital values of the electrical signals are obtained at discrete points in time from said means for sensing;

means for storing the digital values from each channel;

means for centrally controlling the collection, sampling, display and storage of the data collected by the apparatus; and means for simultaneously and in real-time graphically displaying magnitudes of the digital values from each channel as a function of time.

* * * * *